US012774261B2

(12) United States Patent
Fridman et al.

(10) Patent No.: US 12,774,261 B2

(45) Date of Patent: Oct. 27, 2026

(54) PROCESSES AND SYSTEMS FOR ALKANE DEHYDROGENATION

(71) Applicants: Clariant International Ltd, Muttenz (CH); Lummus Technology LLC, Houston, TX (US)

(72) Inventors: Vladimir Fridman, Louisville, KY (US); Sunil Panditrao, Budd Lake, NJ (US)

(73) Assignees: Clariant International Ltd, Muttenz (CH); Lummus Technology LLC, Houston, TX (US)

( * ) Notice: Subject to any disclaimer, the term of this patent is extended or adjusted under 35 U.S.C. 154(b) by 102 days.

(21) Appl. No.: 18/898,091

(22) Filed: Sep. 26, 2024

(65) Prior Publication Data

US 2025/0100955 A1 Mar. 27, 2025

Related U.S. Application Data

(60) Provisional application No. 63/585,468, filed on Sep. 26, 2023.

(51) Int. Cl.
*C07C 5/32* (2006.01)

(52) U.S. Cl.
CPC .................................... *C07C 5/321* (2013.01)

(58) Field of Classification Search
CPC ... C07C 5/321; C07C 5/3332; C07C 2521/04; C07C 2523/24; B01J 8/0285; B01J 8/008; B01J 8/0278; B01J 23/96; B01J 8/02; B01J 23/26; B01J 2208/00513; B01J 2208/025
See application file for complete search history.

(56) References Cited

U.S. PATENT DOCUMENTS

| | | | | |
|---|---|---|---|---|
| 2,419,997 | A | 5/1947 | Houdry | |
| 2,423,029 | A | 6/1947 | Houdry | |
| 6,417,135 | B1 * | 7/2002 | Dyroff | B01J 23/40 502/328 |
| 7,622,623 | B2 | 11/2009 | Fridman | |
| 7,973,207 | B2 | 7/2011 | Fridman | |
| 8,188,328 | B2 | 5/2012 | Fridman | |
| 8,895,797 | B2 * | 11/2014 | Myers | C07C 5/3335 585/654 |
| 9,725,380 | B2 | 8/2017 | Fridman | |

(Continued)

OTHER PUBLICATIONS

International Search Report and Written Opinion in International Patent Application No. PCT/US2024/048640, mailed Mar. 26, 2025.

*Primary Examiner* — Ellen M Mcavoy
(74) *Attorney, Agent, or Firm* — McDonnell Boehnen Hulbert & Berghoff LLP

(57) ABSTRACT

The present disclosure relates generally to processes and systems for dehydrogenating alkanes. The present disclosure relates specifically to processes and systems for dehydrogenating alkanes in which catalyst beds can be cooled rapidly to prevent runaway. In one aspect, a dehydrogenation process includes, when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes.

19 Claims, 2 Drawing Sheets

(56) References Cited

U.S. PATENT DOCUMENTS

| | | | | |
|---|---|---|---|---|
| 2007/0054801 | A1* | 3/2007 | Fridman | B01J 23/26 502/320 |
| 2008/0097134 | A1* | 4/2008 | Fridman | B01J 23/32 585/899 |
| 2011/0245557 | A1* | 10/2011 | Myers | C07C 5/3335 585/312 |
| 2017/0361312 | A1* | 12/2017 | Leal | B01J 21/04 |
| 2021/0276002 | A1* | 9/2021 | Bao | B01J 21/04 |
| 2024/0294446 | A1* | 9/2024 | Diaz Urrutia | B01J 23/60 |
| 2024/0308938 | A1* | 9/2024 | Maduskar | B01J 8/0285 |
| 2024/0327316 | A1* | 10/2024 | Maduskar | B01J 35/615 |

* cited by examiner

PROCESSES AND SYSTEMS FOR ALKANE DEHYDROGENATION

CROSS-REFERENCE TO RELATED APPLICATIONS

This application claims the benefit of priority of U.S. Provisional Patent Application No. 63/585,468, filed Sep. 26, 2023, which is hereby incorporated herein by reference in its entirety.

BACKGROUND OF THE DISCLOSURE

Field

The present disclosure relates to processes for alkane dehydrogenation, as well as systems for the same.

Technical Background

Several endothermic hydrocarbon conversion processes are utilized in commercial operations. These processes include the CATOFIN cyclic fixed bed dehydrogenation process, the fluid bed paraffin dehydrogenation process, the fluid bed ethylbenzene dehydrogenation process, and fluid bed catalytic cracking process, among others. Because these processes are endothermic, heat must be consumed from the surroundings in order for the hydrocarbon conversion reaction to occur. In each of these processes, there is a conversion reaction that is promoted by contacting a hydrocarbon feed with a catalyst. In each of these processes, after a conversion cycle there is at least one reducing and/or oxidizing reaction that refreshes the catalyst for another conversion cycle. Often parallel reactors are used such that there is always at least one reactor that is in a conversion cycle. The heat needed for the endothermic reactions to occur is provided in part by combustion of coke and other undesirable side products that deposit on the catalyst during the conversion process. However, additional heat is typically needed; this is typically provided by hot air or steam that is fed into the catalyst bed from external sources between the hydrocarbon conversion cycles.

As an example, in the typical Houdry dehydrogenation process as taught in U.S. Pat. No. 2,419,997, an aliphatic hydrocarbon passes through a dehydrogenation catalyst bed. As the aliphatic hydrocarbon passes through the catalyst bed, the hydrocarbon is dehydrogenated to its complementary olefin. The olefin is then flushed from the catalyst bed, the catalyst is regenerated to remove deposits like coke by treatment with air, then reduced with hydrogen to provide active catalyst. This cycle is repeated. This dehydrogenation reaction is highly endothermic, and accordingly during the dehydrogenation step the temperature near the inlet of the catalyst bed (where the aliphatic hydrocarbon initially enters the catalyst bed) can decrease by as much as 100° C. This decrease in temperature causes a decrease in hydrocarbon conversion. In addition, during the dehydrogenation step, it is common for coke to form and deposit on the catalyst, further reducing the activity of the catalyst.

In order to reheat the catalyst bed and to remove the coke that has deposited on the catalyst, the reactor is purged of hydrocarbons and then undergoes a regeneration step with air heated to temperatures of up to 700° C. Heat is provided to the bed by the hot air that passes through the bed and also by the exothermicity of the combustion of the coke deposits on the catalyst. Reduction of the catalyst, e.g., with a reducing gas such as hydrogen, prior to the dehydrogenation step also provides some additional heat to the catalyst bed. During regeneration, the hot air flows from the inlet of the catalyst bed to the outlet. This regeneration cycle is normally relatively short, so there is a tendency for the inlet of the bed to be significantly hotter than the outlet of the bed, but because of the timing between cycles in the CATOFIN dehydrogenation process, the catalyst bed does not have time to equilibrate thermally. Thus, the outlet section of the bed remains cooler than the inlet section of the bed as aliphatic hydrocarbons are again fed into the reactor. The high temperature at the inlet of the bed tends to cause formation of undesirable by-products and lower the selectivity and yield of the desired olefin. On the other hand, the lower temperature at the outlet of the bed does not allow full utilization of the catalyst and thus the olefin yield is lower than would be otherwise expected or desired. Also, because the coke distribution in the catalyst bed is not an independently controlled parameter, the heat distribution is also not easily controllable within the bed. Each of these factors affects the resulting catalyst bed temperature profile and makes control of the temperature profile in the bed difficult.

In U.S. Pat. No. 2,423,835, Houdry teaches that the catalyst bed temperature may be controlled within a temperature range suitable for the reactions without requiring an extraneous heating or cooling fluid to be circulated through or around the reaction chamber by including within the catalyst bed "inert" material capable of absorbing or storing up heat which can be subsequently released as required. In commercial practice for fixed bed reactors, this is typically achieved by using a physical mixture of a dehydrogenation catalyst and a granular alpha-aluminum "inert" material as the catalyst bed. However, this process still requires an external heat source.

In more recent years, Clariant has pioneered the use of a so-called "heat-generating material" in a dehydrogenation catalyst bed. The heat-generating material can be physically mixed in with the dehydrogenation catalyst, and is generally catalytically inert with respect to dehydrogenation and side reactions (e.g., cracking or coking), but generates heat under oxidizing and/or reducing reaction conditions. Thus, during the regeneration and/or catalyst reduction steps, the heat-generating material can heat up the catalyst bed, i.e., including dehydrogenation catalyst. Accordingly, while the dehydrogenation catalyst will cool down during the dehydrogenation step, it can be more efficiently heated back up through the use of the heat-generating material.

While the use of heat-generating materials can improve heat utilization, further improvements remain desirable. A challenge remains to provide methods of providing sufficient heat to an endothermic dehydrogenation process without creating uneven heating, while maintaining desirable bed temperatures.

SUMMARY

In one aspect, the present disclosure provides for a process for the dehydrogenation of hydrocarbons, the process comprising:

- providing a dehydrogenation reactor comprising one or more hybrid catalyst beds, each of the one or more hybrid catalyst beds comprising a dehydrogenation catalyst, a heat-generating material, and, optionally, a granular inert material;
- performing the following cycle of steps a plurality of times:

reducing the one or more hybrid catalyst beds by flowing therethrough a reducing stream comprising hydrogen; then contacting the one or more hybrid catalyst beds with an alkane stream by flowing from an upstream direction to a downstream direction, to dehydrogenate the alkane stream to provide an alkene stream, the dehydrogenation being endothermic; then purging the one or more hybrid catalyst beds (e.g., with a steam stream) to substantially remove hydrocarbon therefrom; then contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring a temperature of at least one of the one or more hybrid catalyst beds, wherein at least one of the reducing of the one or more hybrid catalyst beds and the regeneration of the one or more hybrid catalyst beds causes the heat-generating material to generate heat, and wherein the method further includes when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes (e.g., within two minutes, or within a minute).

In another aspect, the disclosure provides a process for the dehydrogenation of hydrocarbons, the process comprising:

providing a dehydrogenation reactor comprising one or more hybrid catalyst beds, each of the one or more hybrid catalyst beds comprising a dehydrogenation catalyst, a heat-generating material, and, optionally, a granular inert material;

performing the following cycle of steps a plurality of times:

reducing the one or more hybrid catalyst beds by flowing therethrough a reducing stream comprising hydrogen; then contacting the one or more hybrid catalyst beds with an alkane stream by flowing from an upstream direction to a downstream direction, to dehydrogenate the alkane stream to provide an alkene stream, the dehydrogenation being endothermic; then purging the one or more hybrid catalyst beds (e.g., with a steam stream) to substantially remove hydrocarbon therefrom; then contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring at least one temperature of at least one of the one or more hybrid catalyst beds, wherein at least one of the reducing of the one or more hybrid catalyst beds and the regeneration of the one or more hybrid catalyst beds causes the heat-generating material to generate heat, and wherein the process further comprises, when the temperature of at least one of the hybrid catalyst beds becomes higher than a first threshold value during a number of consecutive cycles greater than a second threshold value, reducing the temperature of the oxygen-containing stream such that the temperature of the at least one of the hybrid catalyst beds is reduced by at least a third value per cycle (e.g., 2° C. per cycle, e.g., by at least 5° C. per cycle, or at least 10° C. per cycle), for a plurality of cycles.

In another aspect, the present disclosure provides a system for the dehydrogenation of hydrocarbons, the system comprising:

a dehydrogenation reactor comprising one or more hybrid catalyst beds, each of the one or more hybrid catalyst beds comprising a dehydrogenation catalyst, a heat-generating material, and, optionally, a granular inert material, the heat-generating material being configured to generate heat in response to at least one of a reducing of the hybrid catalyst bed in which it is disposed and regeneration of the hybrid catalyst bed in which it is disposed;

a source of a reducing gas stream comprising hydrogen, operatively coupled to the one or more hybrid catalyst beds; and a source of an alkane stream, operatively coupled to the at least one hybrid catalyst bed and configured to flow from an upstream direction to a downstream direction of the dehydrogenation reactor; and a source of an oxygen-containing stream operatively coupled to the one or more hybrid catalyst beds through an operative coupling to the dehydrogenation reactor;

one or more temperature sensors, each independently operatively coupled to one of the one or more hybrid catalyst beds; and a control system configured such that when a temperature of at least one of the hybrid catalyst beds becomes higher than a first threshold value during a number of consecutive cycles greater than a second threshold value, the temperature of the oxygen-containing stream can be reduced (a) by at least 50° C., the reduction of temperature occurring with a temperature drop of at least 50° C. within three minutes (e.g., within two minutes, or within a minute); and/or (b) such that the temperature of the at least one of the hybrid catalyst beds is reduced by at least a third value per cycle (e.g., 2° C. per cycle, e.g., by at least 5° C. per cycle, or at least 10° C. per cycle), for a plurality of cycles.

In another aspect, the present disclosure provides for a system for the dehydrogenation of hydrocarbons, the system comprising:

a dehydrogenation reactor comprising one or more hybrid catalyst beds, each of the one or more hybrid catalyst beds comprising a dehydrogenation catalyst, a heat-generating material, and, optionally, a granular inert material, the heat-generating material being configured to generate heat in response to at least one of a reducing of the hybrid catalyst bed in which it is disposed and regeneration of the hybrid catalyst bed in which it is disposed;

a source of a reducing gas stream comprising hydrogen, operatively coupled to the one or more hybrid catalyst beds; and a source of an alkane stream, operatively coupled to the at least one hybrid catalyst bed and configured to flow from an upstream direction to a downstream direction of the dehydrogenation reactor; and a source of a hotter oxygen-containing substream and a source of a colder oxygen-containing substream, each operatively coupled to the one or more hybrid catalyst beds through operative coupling to the dehydrogenation reactor, configured to allow for a selection of a variable flow ratio of the hotter oxygen-containing substream to the colder oxygen-containing substream.

Other aspects of the disclosure will be apparent to those skilled in the art in view of the description that follows.

DETAILED DESCRIPTION

Figure 1:
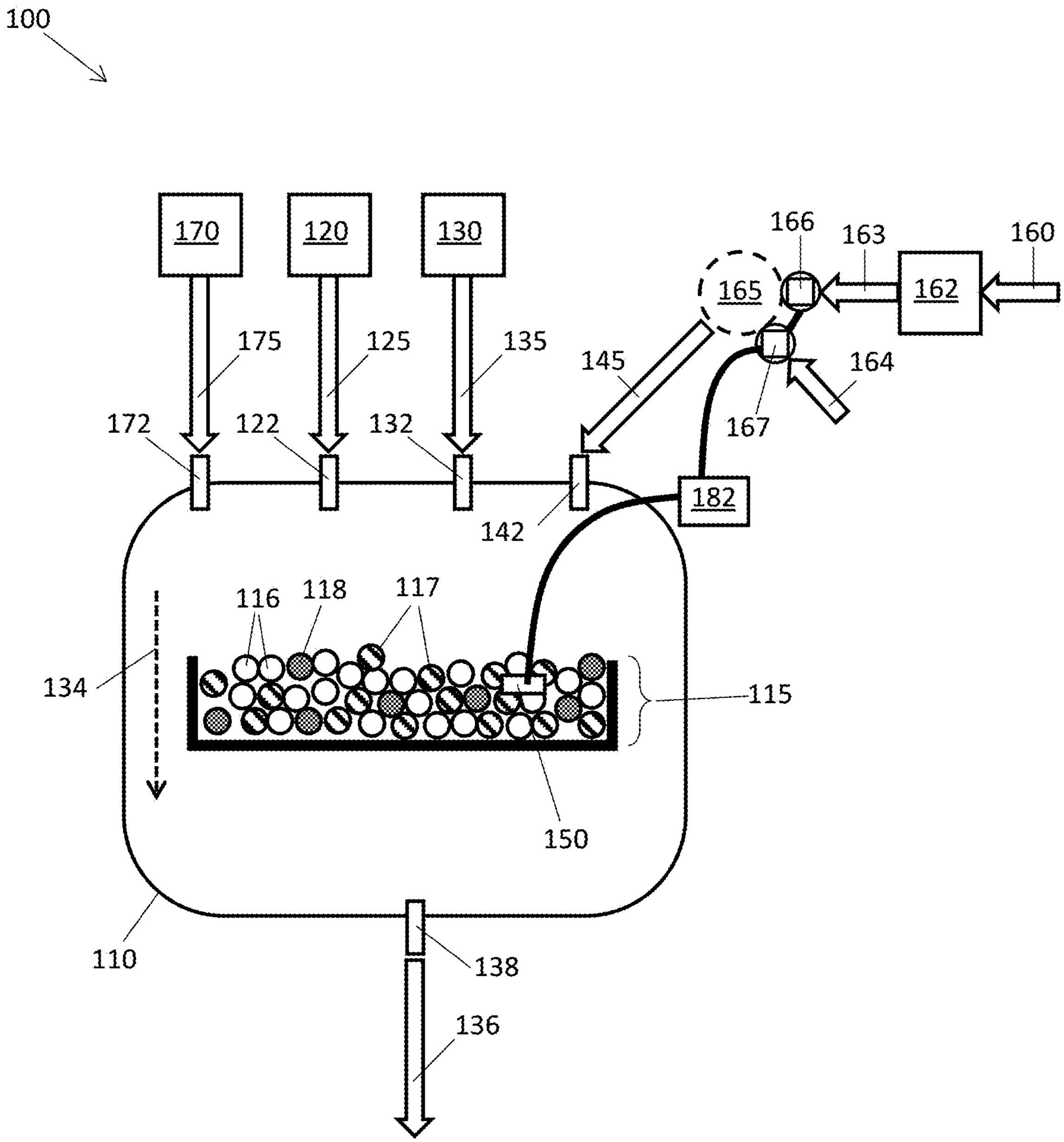
FIG. 1 provides a schematic view of an embodiment of a system and process according to the disclosure.

The present inventors have developed a process for the improved control of catalyst bed temperature during alkane dehydrogenation.

The conventional light paraffin dehydrogenation process was developed by Houdry US, and is conventionally based on fixed-bed $CrO_x/Al_2O_3$ catalysts operating in parallel, adiabatic, fixed-bed reactors operating in a cyclic mode. This process is described, for example, in U.S. Pat. Nos. 2,419,997 and 2,423,029, each of which is hereby incorporated herein by reference in its entirety. In typical operation, the cycle starts with the reduction of the catalyst bed by a mixture of $H_2$ and light hydrocarbons. Subsequently, dehydrogenation of an alkane feed takes place under vacuum. After dehydrogenation, the reactor and catalyst bed is steam purged to substantially remove hydrocarbons, and then regenerated and reheated by hot air. Finally, the reactor is evacuated to complete the cycle.

Regeneration is important, as it not only cleans deposits off of the dehydration catalyst, but it also provides heat that can be consumed by a subsequent endothermic dehydrogenation reaction. Importantly, the level of paraffin conversion has been found to depend on dehydrogenation catalyst temperature, and thus on the efficiency of the heat supply during regeneration. Heat can be supplied by at least two mechanisms, including the exothermic reaction of coke burning, and direct heat transfer from the heated air used in the regeneration. Heated air can be provided at a temperature up to 680° C. in some instances, and fuel gas may be added to the hot air in order to further increase the effective temperature in the reactor to 730° C. Heat is can also typically added to the catalyst in reduction step, by the exothermicity of the reduction of high oxidation state chromium.

The present inventors have noted that provision of heat through the introduction of hot air can have a disadvantage in uneven catalyst heating. At the regeneration time is relatively short, on the order of minutes (e.g., 4-12 minutes), the heated air mainly provides heat to the top of the catalyst bed. For example, it has been presently found that the provision of heat through heated air alone can result in a temperature at the top of the catalyst bed of 650-660° C., while the bottom is only 560-570° C., for air introduced at 730° C.

In order to improve the heat input and distribution to the catalyst bed, a heat-generating material can be used. As described above, the heat-generating material is generally catalytically inert with respect to dehydrogenation and side reactions, such as cracking or coking, but, critically, generates heat upon being exposed to oxidizing and/or reducing oxidizing reaction conditions. The heat-generating material can be mixed with the dehydrogenation catalyst, and, during the regeneration and/or reduction steps, heat up to provide heat to the dehydrogenation catalyst. Thus, the heat-generating material can help maintain desirably high catalyst bed temperatures over multiple cycles. it has been found that the use of heat-generating material can increase yields and save energy while simultaneously reducing emissions. Heat-generating materials and their uses in cyclic dehydrogenation processes are described, for example, in U.S. Pat. Nos. 7,622,623, 7,973,207, and 8,188,328, and U.S. Patent Application Publication no. 2023/0090285, each of which is hereby incorporated herein by reference in its entirety, for example, for teachings regarding heat-generating materials and cyclic dehydrogenation processes using the same.

The present inventors have noted that a heat-generating material typically provides more heat to the second half of the catalyst bed, and the amount added is adjusted based on the heat utilization within the catalyst bed. In conventional processes, the amount is typically limited to 10% to 35% of the total catalyst bed. It has been presently estimated that the total heat input in these cases from the heat-generating material ranges from approximately 20-40%, while the contribution of heat from heated regeneration air ranges from 40-60%. In these cases, the air inlet temperature can be used to effectively control the catalyst bed temperature, as the majority of the heat input comes from the air input.

However, the present inventors have noted that it is desired to be able to increase the proportion of the heat-generating material supplied to the catalyst bed, thereby increasing thermal efficiency and further reducing emissions by reducing the need for heating of the air (or other oxygen-containing stream) used in regeneration. An increase in the proportion of the heat-generating material to 50% and higher, for example, will increase the heat input from the heat-generating material from 20-40% as estimated below to an estimated 60-80%.

The present inventors have determined that, with larger proportion of heat coming from the heat-generating material, a relatively smaller amount of thermal energy will come from the air inlet, and temperature control at the air inlet would be generally less effective at controlling bed temperature. This is especially true in cases where the temperature control of the air inlet is performed, as is conventional, by adjusting the temperature of the heater that heats the air used in regeneration. In such cases, the relatively slow decrease in temperature of the air may be insufficient to address a situation where the catalyst bed temperature is spiking due to high heat generation by a heat-generating material.

In order to address this issue, the present inventors have determined that it is desirable to be able to rapidly drop the temperature of the regeneration air introduced to the catalyst bed, especially in cases when relatively more heat-generating material is used. There are a number of ways to do this, as the person of ordinary skill in the art will appreciate. But it has been presently determined that in some embodiments a source of colder air (or other oxygen-containing gas) can be provided to help drop the temperature of the regeneration gas. The cold air can be mixed with the hot air to reduce its temperature before it is admitted into the reactor, or can injected directly into the reactor along with the hot air. Regardless of the method used, a relatively rapid, controllable drop of the temperature of the regeneration air can be used to more quickly cool the catalyst bed and control catalyst bed temperatures in the case of excess thermal energy being provided to the catalyst bed. This approach advantageously allows for increased heat-generating material loading without compromising reactor temperature control and the risk of runaway.

Accordingly, in one aspect, the present disclosure provides for a process for the dehydrogenation of hydrocarbons, the process comprising:

providing a dehydrogenation reactor comprising one or more hybrid catalyst beds, each of the one or more hybrid catalyst beds comprising a dehydrogenation catalyst, a heat-generating material, and, optionally, a granular inert material;

performing the following cycle of steps a plurality of times:

reducing the one or more hybrid catalyst beds by flowing therethrough a reducing stream comprising hydrogen; then contacting the one or more hybrid catalyst beds with an alkane stream by flowing from an upstream direction to a downstream direction, to dehydrogenate the alkane stream to provide an alkene stream, the dehydrogenation being endothermic; then purging the one or more hybrid catalyst beds (e.g., with a steam stream) to substantially remove hydrocarbon therefrom; then contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring at least one of a temperature of at least one of the one or more hybrid catalyst beds, wherein at least one of the reducing of the one or more hybrid catalyst beds and the regeneration of the one or more hybrid catalyst beds causes the heat-generating material to generate heat, and wherein the process further includes, when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes (e.g., within two minutes, or within a minute).

And in another aspect, the disclosure provides a process for the dehydrogenation of hydrocarbons, the process comprising:

providing a dehydrogenation reactor comprising one or more hybrid catalyst beds, each of the one or more hybrid catalyst beds comprising a dehydrogenation catalyst, a heat-generating material, and, optionally, a granular inert material;

performing the following cycle of steps a plurality of times:

reducing the one or more hybrid catalyst beds by flowing therethrough a reducing stream comprising hydrogen; then contacting the one or more hybrid catalyst beds with an alkane stream by flowing from an upstream direction to a downstream direction, to dehydrogenate the alkane stream to provide an alkene stream, the dehydrogenation being endothermic; then purging the one or more hybrid catalyst beds (e.g., with a steam stream) to substantially remove hydrocarbon therefrom; then contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring at least one temperature of at least one of the one or more hybrid catalyst beds, wherein at least one of the reducing of the one or more hybrid catalyst beds and the regeneration of the one or more hybrid catalyst beds causes the heat-generating material to generate heat, and wherein the process further comprises, when the temperature of at least one of the hybrid catalyst beds becomes higher than a first threshold value during a number of consecutive cycles greater than a second threshold value, reducing the temperature of the oxygen-containing stream such that the temperature of the at least one of the hybrid catalyst beds is reduced by a third value per cycle (e.g., by at least 2° C. per cycle, e.g., by at least 5° C. per cycle, or at least 10° C. per cycle), for a plurality of cycles.

In another aspect, the present disclosure provides a system for the dehydrogenation of hydrocarbons, the system comprising:

a dehydrogenation reactor comprising one or more hybrid catalyst beds, each of the one or more hybrid catalyst beds comprising a dehydrogenation catalyst and a heat-generating material, the heat-generating material being configured to generate heat in response to at least one of a reducing of the hybrid catalyst bed in which it is disposed and regeneration of the hybrid catalyst bed in which it is disposed;

a source of a reducing gas stream comprising hydrogen, operatively coupled to the one or more hybrid catalyst beds; and a source of an alkane stream, operatively coupled to the at least one hybrid catalyst bed and configured to flow from an upstream direction to a downstream direction of the dehydrogenation reactor; and a source of an oxygen-containing stream operatively coupled to the one or more hybrid catalyst beds, through an operative coupling to the dehydrogenation reactor;

one or more temperature sensors, each independently operatively coupled to one of the one or more hybrid catalyst beds; and a control system configured such that when a temperature of at least one of the hybrid catalyst beds becomes higher than a first threshold value as measured by at least one of the one or more temperature sensors during a number of consecutive cycles greater than a second threshold value, the temperature of the oxygen-containing stream at the first input by can be reduced (a) by at least 50° C., the reduction of temperature occurring with a temperature drop of at least 50° C. within three minutes (e.g., within two minutes, or within a minute); and/or (b) such that the temperature of the at least one of the hybrid catalyst beds is reduced by a third value per cycle (e.g., at least 2° C. per cycle, e.g., by at least 5° C. per cycle, or at least 10° C. per cycle), for a plurality of cycles.

The system according to this aspect can be used, for example, to perform the methods described herein.

In another aspect, the present disclosure provides for a system for the dehydrogenation of hydrocarbons, the system comprising:

a dehydrogenation reactor comprising one or more hybrid catalyst beds, each of the one or more hybrid catalyst beds comprising a dehydrogenation catalyst and a heat-generating material, the heat-generating material being configured to generate heat in response to at least one of a reducing of the hybrid catalyst bed in which it is disposed and regeneration of the hybrid catalyst bed in which it is disposed;

a source of a reducing gas stream comprising hydrogen, operatively coupled to the one or more hybrid catalyst beds; and a source of an alkane stream, operatively coupled to the at least one hybrid catalyst bed and configured to flow from an upstream direction to a downstream direction of the dehydrogenation reactor; and a source of a hotter oxygen-containing substream and a source of a colder oxygen-containing substream, each operatively coupled to the one or more hybrid catalyst beds through operative coupling to the dehydrogenation reactor, configured to allow for a selection of a variable flow ratio of the hotter oxygen-containing substream to the colder oxygen-containing substream.

The system according to this aspect can be used, for example, to perform the methods described herein.

One example is shown in schematic view in FIG. 1. Here a system 100 for the dehydrogenation of hydrocarbons includes a dehydrogenation reactor 110, that includes one or more (here, one) hybrid catalyst beds 115. As used herein, a "hybrid" catalyst bed that includes both a dehydrogenation catalyst (e.g., 116 in FIG. 1) and a heat-generating material (e.g., 117 in FIG. 1), and can optionally include a granular inert material 118, as described in more detail below. The heat-generating material is configured to generate heat in response to at least one of a reducing of the hybrid catalyst bed in which it is disposed and regeneration of the hybrid catalyst bed in which it is disposed. A source 120 of a reducing gas stream 125 is operatively coupled to the hybrid catalyst bed 115, here, through coupling to the reactor 110 at reducing gas inlet 122 thereof. A source 130 of an alkane stream 135 is operatively coupled to the hybrid catalyst bed 115, here, through coupling to the reactor 110 at alkane stream inlet 132 thereof. A source of an oxygen-containing stream 145 is operatively coupled to the hybrid catalyst bed 115, here, through coupling to the reactor 110 at oxygen-containing stream inlet 142 thereof. In various embodiments, and as shown in FIG. 1, a source 170 of a steam stream 175 is operatively coupled to the hybrid catalyst bed 115, here through coupling to the reactor 110 at steam stream inlet 172 thereof.

In various embodiments, in order to help provide for temperature control, the system further includes one or more temperature sensors 150, each independently operatively coupled to one of the hybrid catalyst beds 115. The person of ordinary skill in the art will appreciate that the one or more temperature sensors can be positioned to measure temperature at a variety of areas of a catalyst bed at a variety of positions, be they upstream, downstream or central (e.g., at the top of the hybrid catalyst bed, at the bottom of the hybrid catalyst bed, or at a central portion of the hybrid catalyst bed shown in FIG. 1).

In one embodiment of process for dehydrogenating hydrocarbons of the disclosure, a dehydrogenation reactor 110 comprising one or more (here, one) hybrid catalyst beds 115, each comprising a dehydrogenation catalyst 116, a heat-generating material 117, and optionally a granular inert material 118 is provided. The process includes performing a cycle of steps a plurality of times. The cycle includes, in a reducing step, reducing the one or more (here, one) hybrid catalyst beds 115 by flowing therethrough a reducing stream comprising hydrogen, here, by introduction through reducing gas inlet 122. Then, in a dehydrogenation step, the one or more (here, one) hybrid catalyst beds 115 are contacted with an alkane stream, here, by introduction through alkane stream inlet 132 by flowing from an upstream direction to a downstream direction (as indicated by arrow 134), to dehydrogenate the alkane stream to provide an alkene stream 136, which can be removed from the reactor at outlet 138 thereof. Notably, the dehydrogenation is endothermic. As described above, the endothermicity of the dehydrogenation can cause the temperature of the hybrid catalyst bed to decrease, which undesirably affects dehydrogenation catalyst performance. Coke and other side reaction products can also collect on the dehydrogenation catalyst, which also undesirably affects dehydrogenation catalyst performance. Accordingly, after the hybrid catalyst bed is purged to substantially remove hydrocarbons, for example, at least 50 wt %, or at least 75 wt %, or at least 90 wt %, (e.g., with a steam stream 175 from steam source 170 admitted to the reactor at steam stream inlet 172), the next step is a regeneration step. In the regeneration step, the one or more hybrid catalyst beds 115 are contacted with an oxygen-containing stream 145 by introducing the oxygen-containing stream to the dehydrogenation reactor (here, through oxygen-containing stream inlet 142). This regeneration step is performed at a first temperature sufficient to regenerate the one or more hybrid catalyst beds, for example, by removing a substantial degree (e.g., at least 50 wt %, or at least 75 wt %, or at least 90 wt %) of coke and other deposits, and by substantially increasing the temperature of the one or more hybrid catalyst beds. This can be performed while monitoring at least one of a temperature of at least one of the one or more hybrid catalyst beds, e.g., using temperature sensor 150. Notably, at least one of the reducing of the one or more hybrid catalyst beds and the regeneration of the one or more hybrid catalyst beds causes the heat-generating material to generate heat.

The present inventors have noted that, in some cases, it can be desirable to provide for a relatively rapid cooling of the one or more hybrid catalyst beds. This can be especially desirable, e.g., when the one or more hybrid catalyst beds has a relatively high volume fraction of heat-generating material, e.g., at least 40 wt %. However, such rapid temperature control can be desirable in a variety of other configurations.

Accordingly, in various embodiments of processes of the disclosure, the process further includes, when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes (e.g., within two minutes, or within a minute). Such rapid decrease in the temperature of the oxygen-containing stream can help to better control hybrid catalyst bed temperatures, especially in cases of a relatively large heat contribution by a heat-generating material.

And in various embodiments as otherwise described herein, the process further includes, when the temperature of at least one of the hybrid catalyst beds becomes higher than a first threshold value during a number of consecutive cycles greater than a second threshold value, reducing the temperature of the oxygen-containing stream such that the temperature of the at least one of the hybrid catalyst beds is reduced by at least a third value per cycle (e.g., 2° C. per cycle, e.g., by at least 5° C. per cycle, or at least 10° C. per cycle), for a plurality of cycles. The person of ordinary skill in the art can select a desired third value based on particular system, to allow the system to remain operating at a desirable temperature. Of course, for longer term control, the temperature of the heater for the oxygen-containing gas can be controlled—but the methods and systems of the present disclosure can be used to provide cooling of catalyst beds more rapidly than might be convenient when heater control is not sufficiently fast. The person of ordinary skill in the art can provide a sufficiently rapid decrease in the temperature of the oxygen-containing stream can be selected to provide such decreases in the temperature of the one or more hybrid catalyst beds at issue.

The person of ordinary skill in the art will appreciate that the first threshold value, the second threshold value and the third value can vary based upon system parameters, and thus can be selected by the person of ordinary skill in the art based on the disclosure herein in view of the particular system being used.

In various embodiments of all of the methods and systems as described herein, the first threshold value is at least 500° C., e.g., in the range of 500-1100° C. For example, in various embodiments, the first threshold value is in the range of 500-1050° C., or 500-1000° C., or 500-950° C., or 500-900° C., or 500-850° C., or 500-800° C., or 500-750° C., or 500-700° C., or 500-650° C., or 500-600° C. In various embodiments of all of the methods and systems as described herein, the first threshold value is at least 550° C., e.g., in the range of 550-1100° C. For example, in various embodiments, the first threshold value is in the range of 550-1050° C., or 550-1000° C., or 550-950° C., or 550-900° C., or 550-850° C., or 550-800° C., or 550-750° C., or 550-700° C., or 550-650° C. In various embodiments of all of the methods and systems as described herein, the first threshold value is at least 600° C., e.g., in the range of 600-1100° C. For example, in various embodiments, the first threshold value is in the range of 600-1050° C., or 600-1000° C., or 600-950° C., or 600-900° C., or 600-850° C., or 600-800° C., or 600-750° C., or 600-700° C. In various embodiments of all of the methods and systems as described herein, the first threshold value is at least 600° C., e.g., in the range of 600-1100° C. For example, in various embodiments, the first threshold value is in the range of 600-1050° C., or 600-1000° C., or 600-950° C., or 600-900° C., or 600-850° C., or 600-800° C., or 600-750° C., or 600-700° C. In various embodiments, the first threshold value is at least 650° C., for example, in the range of 650-1100° C., e.g., 650-1050° C., or 650-1000° C., or 650-950° C., or 650-900° C., or 650-850° C., or 650-800° C., or 650-750° C. In various embodiments, the first threshold value is at least 700° C., for example, in the range of 700-1100° C., e.g., 700-1050° C., or 700-1000° C., or 700-950° C., or 700-900° C., or 700-850° C., or 700-800° C. In various embodiments, the first threshold value is at least 750° C., for example, in the range of 750-1100° C., e.g., 750-1050° C., or 750-1000° C., or 750-950° C., or 750-900° C., or 750-850° C. In various embodiments, the first threshold value is at least 800° C., for example, in the range of 800-1100° C., e.g., 800-1050° C., or 800-1000° C., or 800-950° C., or 800-900° C. In various embodiments, the first threshold value is at least 850° C., for example, in the range of 850-1100° C., e.g., 850-1050° C., or 850-1000° C., or 850-950° C.

The person of ordinary skill in the art will appreciate that in many cases, a single cycle with a temperature above the first threshold value is not a sign of imminent runaway risk. Rather, runaway risk is heightened when catalyst bed temperature is above a first threshold value (e.g., as described above) for a consecutive number of cycles that is greater than a second threshold value. In various embodiments of the methods and systems as described herein, the second threshold value is at least 5, e.g., at least 7. In various embodiments, the second threshold value is at least 10, e.g., at least 20. In various embodiments of the methods and systems as described herein, the second threshold value is no more than 100, e.g., no more than 75. In various embodiments, the second threshold value is no more than 50, e.g., no more than 25. For example, in various embodiments, the second threshold value is in the range of 5-100, e.g., in the range of 5-75, or 5-50, or 5-25, or 7-100, or 7-75, or 7-50, or 7-35, or 10-100, or 10-75, or 10-50, or 10-25, or 20-100, or 20-75, or 20-50.

The third value can vary. In various embodiments, the third value is at least 2° C., e.g., in the range of 0.2-50° C., or 2-30° C., or 2-15° C., or 2-10° C., or 2-5° C. In various embodiments, the third value is at least 5° C., e.g., in the range of 0.5-50° C., or 5-30° C., or 5-15° C., or 5-10° C. In various embodiments, the third value is at least 10° C., e.g., in the range of 10-50° C., or 10-30° C., or 10-20° C.

The person of ordinary skill in the art will appreciate that the temperature of the oxygen-containing stream can be rapidly decreased in a number of ways. The present inventors have noted that in conventional systems, the oxygen-containing gas (typically air) used for the regeneration is heated using a heater. This can be effective to efficiently heat the oxygen-containing gas, and to provide fine temperature control, but the response of such a heater is relatively slow, so that it can be difficult to drop the temperature of the oxygen-containing stream quickly. The present inventors have noted that in systems and methods where heater control is not sufficient to provide a rapid drop in temperature, a colder oxygen-containing gas can be provided and, when necessary, mixed with the heated oxygen-containing stream to cool it rapidly.

Accordingly, in various embodiments, the system includes (e.g., as the source of the oxygen-containing stream) a source of a hotter oxygen-containing substream and a source of a colder oxygen-containing substream, each operatively coupled to the one or more hybrid catalyst beds through operative coupling to the dehydrogenation reactor, configured to allow for a selection of a variable flow ratio of the hotter oxygen-containing substream to the colder oxygen-containing substream.

As used herein, an "oxygen-containing stream" is defined as the entirety of the oxygen-containing gas input to the dehydrogenation reactor during the regeneration. As would be understood by a person of ordinary skill in the art, the entire oxygen-containing stream can be provided to the reactor at a single inlet. For example, in the embodiment of FIG. 1, oxygen-containing stream 145 is introduced to the dehydrogenation reactor at oxygen-containing stream inlet 142. For example, a first input stream comprising oxygen can be heated (e.g., using a heater, such as a gas-fired heater), then the resulting hotter oxygen-containing substream can be used as at least a portion of the oxygen-containing stream. This can be used as substantially all (or even all) of the oxygen-containing stream during normal operation. For example, in various embodiments the hotter air stream makes up at least 90 wt % (e.g., at least 95 wt % or at least 99 wt %) of the oxygen-containing stream during at least one stage of the regeneration, for example, during at least one period in which the monitored temperature of the one or more hybrid catalyst bed is below the first threshold value.

As described above, when the temperature of at least one of the one or more hybrid catalyst bed rises above a first threshold value, it can be desirable to quickly decrease the temperature of the oxygen-containing stream. The present inventors have noted that this can be done by adding a colder oxygen-containing substream to the hotter oxygen-containing substream. Accordingly, in various embodiments, the reduction of the temperature of the oxygen-containing stream comprises admixing with the hotter oxygen-containing substream a colder oxygen-containing substream having a temperature substantially lower than the temperature of the hotter oxygen-containing stream, for example, as described below.

The present inventors have noted that rapid temperature reduction of the oxygen-containing stream can be effected by mixing a plurality of substreams that are mixed before reactor introduction. Accordingly, in various embodiments of the processes as described herein, the hotter oxygen-containing substream and the colder oxygen-containing substream are admixed before introduction to the reactor. This is shown in the schematic view of FIG. 1. Here, a first input stream 160 including oxygen is heated (here, in heater 162) to provide a hotter oxygen-containing substream 163. A colder oxygen-containing substream 164 is provided, bypassing the heater 162, and being admixed with the hotter oxygen-containing substream in mixing zone 165. The mixing zone can merely be a junction of the conduits carrying the gases, but the person of ordinary skill in the art will appreciate that a gas mixer or gas blender can be used. One or more valves 166 and 167 can be used to control the flow ratio of the hotter oxygen-containing substream to the colder oxygen-containing substream, and thus control the temperature of the oxygen-containing stream at the dehydrogenation reactor inlet (e.g., in FIG. 1, at oxygen-containing stream inlet 142). For example, during operation, valve **166*a* can be open and valve 166 can be closed, so as to provide only the hotter oxygen-containing substream to the reactor. When the temperature of a hybrid catalyst bed rises above the first threshold value during a number of consecutive cycles greater than the second threshold value, valve 167 can be at least partially opened (and, optionally, valve 166 can be at least partially closed) to mix in the colder oxygen-containing stream and reduce the temperature of the oxygen-containing stream. In various embodiments the colder oxygen-containing substream can be provided by splitting off a portion of the first input stream 160** and refraining from substantially heating it; alternatively the split-off portion can be heated, but to a substantially lower temperature than the hotter oxygen-containing substream. Here, too, the hotter oxygen-containing substream and the colder oxygen-containing substream are provided from a common oxygen-containing gas source.

Figure 2:
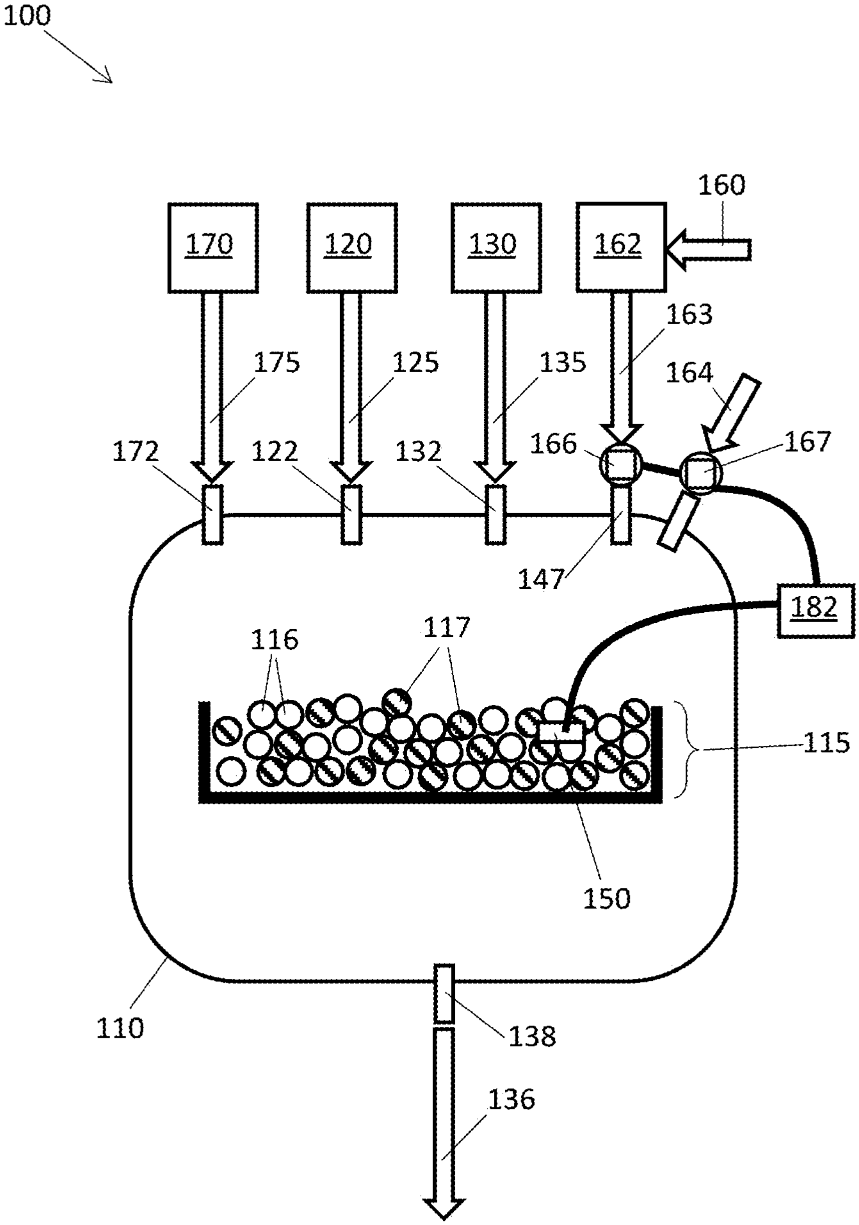
FIG. 2 provides a partial schematic view of an embodiment of a system and process according to the disclosure.

Alternatively the oxygen-containing stream can be provided as a plurality of substreams that are introduced to the reactor in parallel. In such cases, the temperature of the oxygen-containing stream is deemed to be the average temperature of all such substreams, averaged for pressure and volume so as provide a temperature contribution were the substreams combined before introduction to the dehydrogenation reactor. Such a configuration is shown in the schematic view of FIG. 2. Here, hotter oxygen-containing substream 163 can be provided by a heater 162 which heats an oxygen-containing gas (e.g., air, from source 160), and introduced to the dehydrogenation reactor 110 at a first substream inlet 147. A separate colder oxygen-containing substream 164 is introduced separately to the dehydrogenation reactor at a second substream inlet 148. Valves 166 and 167 can be used to control the flow ratio to provide a desired reduction of temperature to the overall oxygen-containing stream 1 (i.e., the combination of hotter and colder oxygen-containing substreams 163 and 164). For example, during operation, valve 166 can be open and valve 167 can be closed, so as to provide only the hotter oxygen-containing substream to the reactor. When the temperature of a hybrid catalyst bed rises above the first threshold value during a number of consecutive cycles greater than the second threshold value, valve 167 can be at least partially opened (and, optionally, valve 166 can be at least partially closed) to introduce the colder oxygen-containing stream to the reactor and reduce the temperature of the overall oxygen-containing stream.

These configurations are different than the conventional configuration, in which the air (or other oxygen-containing gas) for regeneration is heated by a heater on its way to the reactor, without provision of a separate colder air source. Accordingly, in such conventional configurations the temperature of the regeneration air can be controlled only by controlling the heater, which can be effective for fine control, but is generally less effective for fast temperature changes.

As the person of ordinary skill in the art will appreciate, the oxygen-containing stream used in the regeneration is desirably rather hot, so as to provide for substantially complete combustion of coke and other deposits, and to provide for desirable heating of the dehydrogenation catalyst. For example, in various embodiments as otherwise described herein, the oxygen-containing stream during at least one stage of the regeneration, has a temperature in the range of 500° C. to 800° C. (e.g., in the range 550° C. to 800° C., or 600° C. to 800° C., or 500° C. to 750° C., or 500° C. to 700° C.). This can be the case, for example, during at least one period in which the monitored temperatures of the one or more hybrid catalyst bed is below the first threshold value. During such time, it can be desirable to maintain a relatively high temperature of the oxygen-containing stream.

However, as described above, it can be desirable to rapidly reduce the temperature of the oxygen-containing stream, for example, when a temperature of at least one of the hybrid catalyst beds becomes higher than a first threshold value (e.g., as measured by at least one of the one or more temperature sensors) during a number of consecutive cycles greater than a second threshold value. Thus, various processes described herein further include, when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes (e.g., within two minutes, or within a minute). In various embodiments, the reduction of the temperature of the oxygen-containing stream is at least 75° C., the reduction of temperature occurring with a temperature drop of at least 75° C. within three minutes (e.g., within two minutes, or within a minute). In various embodiments, the reduction of the temperature of the oxygen-containing stream is at least 100° C., the reduction of temperature occurring with a temperature drop of at least 100° C. within three minutes (e.g., within two minutes, or within a minute). The person of ordinary skill in the art can determine, for a given system, the appropriate temperature reduction of the oxygen-containing stream to provide a desired temperature reduction of a hybrid catalyst bed.

The person of ordinary skill in the art can select temperatures of the hotter and colder oxygen-containing substreams, when used, to provide a desired temperature reduction. As described above, the hotter oxygen-containing substream can, in various embodiments, be used to provide most, or even all, of the oxygen-containing stream during various stages of operation, e.g., when the which the monitored temperatures of the one or more hybrid catalyst bed is below the first threshold value. Accordingly, in various embodiments as otherwise described herein, the temperature of the hotter oxygen-containing substream is in the range of 500° C. to 800° C. (e.g., in the range 550° C. to 800° C., or 600° C. to 800° C., or 500° C. to 750° C., or 500° C. to 700° C.). The colder oxygen-containing substream, as it is used to provide cooling, can be at a much lower temperature, e.g., at least 50° C. colder than the hotter oxygen-containing substream, such as at least 100° C. colder, or at least 200° C. colder. For example, in various embodiments as otherwise described herein, the temperature of the colder oxygen-containing substream is in the range of −20° C. to 250° C., for example, in the range of 0° C. to 200° C., or 0° C. to 100° C., or 0° C. to 50° C. It can be desirable to use a source at atmospheric temperature.

While manual control can be used to perform the reduction of temperature, the person of ordinary skill in the art will appreciate that this can be automated using conventional techniques. Accordingly, in various embodiments of the disclosure, the a control system configured such that when a temperature of at least one of the hybrid catalyst beds becomes higher than a first threshold value as measured by at least one of the one or more temperature sensors during a number of consecutive cycles greater than a second threshold value, the temperature of the oxygen-containing stream at the first input by can be reduced at least 50° C., the reduction of temperature occurring with a temperature drop of at least 50° C. within three minutes (e.g., within two minutes, or within a minute). In various embodiments of the systems as otherwise described herein, the control system is configured such that when the temperature of at least one of the hybrid catalyst beds becomes higher than the first threshold value, the temperature of the oxygen-containing stream can be reduced by at least 75° C., the reduction of temperature occurring with a temperature drop of at least 75° C. within three minutes (e.g., within two minutes, or within a minute). In various embodiments of the systems as otherwise described herein, the control system is configured such that when the temperature of at least one of the hybrid catalyst beds becomes higher than the first threshold value, the temperature of the oxygen-containing stream can be reduced by at least 100° C., the reduction of temperature occurring with a temperature drop of at least 100° C. within three minutes (e.g., within two minutes, or within a minute). The person of ordinary skill in the art can provide an appropriate control system, which is typically includes a computer-based controller, and one or more controllable system components such as valves, thermostat controls, and pumps that that can be operated provide the desired temperature drop. An example of a control system is shown in FIG. 1; here, the control system includes controller 182, which is operatively coupled to valves 166 and 167 as well as to temperature sensor 150. The controller can receive a temperature reading from the temperature sensor, and appropriate control the valves 166 and 167 to provide temperature control of the oxygen-containing stream as described herein.

Alkane dehydrogenation, in general, is an endothermic process, so it is desirable to add thermal energy to the process in order to maintain a particular desired operating temperature. Accordingly, in various embodiments as otherwise described herein, in each cycle the regeneration and the reduction steps together are sufficient to introduce an amount of thermal energy to the dehydrogenation approximately equal to the energy consumption of the endothermic dehydrogenation step. For example, in particular embodiments, in a plurality of the cycles, the regeneration and the reduction steps are sufficient to raise the temperatures of the one or more hybrid catalyst beds by at least 90% of the temperature loss during the preceding dehydrogenation step, e.g., at least 95% of the temperature loss during the preceding dehydrogenation step, or at least 98% of the of the temperature loss during the preceding dehydrogenation step.

As described above, the one or more hybrid catalyst beds include heat-generating material that can introduce thermal energy in the regeneration and/or reduction steps, e.g., through chemical reaction. In various embodiments as otherwise described herein, the heat-generating material generates heat during one or both of the regeneration and reduction steps (e.g., at least during the regeneration step). In various embodiments, the heat generated by the heat-generating material during the reduction and/or regeneration steps contributes at least 40% of the heat energy consumed in the endothermic dehydrogenation reaction (e.g., at least 50%, or at least 60%). For example, in various embodiments, the heat generated by the heat-generating material during the reduction and/or regeneration steps contributes in the range of 40-85% of the heat energy consumed in the endothermic dehydrogenation reaction (e.g., in the range of 40-80%, or 40-75%, or 40-70%, or 50-85%, or 50-80%, or 50-75%, or 50-70%, or 60-85%, or 50-80%, or 50-75%).

Of course, thermal energy can also be provided by heat transfer from the oxygen-containing stream, which is typically provided at elevated temperature. In various embodiments, the heat energy provided to the one or more hybrid catalyst beds by the heat-generating material during the regeneration step is at least 40% of the total heat energy provided to the one or more hybrid catalyst beds by the heat-generating material and the oxygen-containing stream during the regeneration step (e.g., at least 50%, or at least 60%). In various embodiments, the heat energy provided to the one or more hybrid catalyst beds by the heat-generating material during the regeneration step is in the range of 40-85% of the total heat energy provided to the one or more hybrid catalyst beds by the heat-generating material and the oxygen-containing stream during the regeneration step (e.g., in the range of 40-80%, or 40-75%, or 40-70%, or 50-85%, or 50-80%, or 50-75%, or 50-70%, or 60-85%, or 50-80%, or 50-75%).

While the oxygen-containing gas can itself be provided at high temperature, it can also include a fuel gas that can combust in the one or more hybrid catalyst beds and provide additional heat energy. For the purposes of the calculations above, heat from combustion of a fuel gas is considered to be heat provided by the oxygen-containing stream.

Notably, the present inventors have determined that the ability to rapid cool the one or more hybrid catalyst beds is especially important when relatively high amounts of heat-generating materials are present. In conventional systems, the amount of heat-generating material is only on the order of 10-35 wt % of the combined amount of heat-generating material and dehydrogenation catalyst. But it can be desirable to increase this amount; in such cases, relatively more heat is provided by the heat-generating material, and relatively small changes in the temperature of the oxygen-containing stream during regeneration will have relatively smaller effect. Thus, the processes and systems described herein are especially desirable for use in systems with higher amounts of heat-generating materials. Accordingly, in various embodiments as otherwise described herein, one or more of (e.g., each of) the one or more hybrid catalyst beds includes heat-generating material in an amount that is at least 40 wt % of the combined amount of heat-generating material and dehydrogenation catalyst, e.g., at least 45 wt %, or at least 50 wt %. In various embodiments, one or more of (e.g., each of) the one or more hybrid catalyst beds includes heat-generating material in an amount in the range of 40-70 wt % of the combined amount of heat-generating material and dehydrogenation catalyst, e.g., 40-65 wt %, or 40-60 wt %, or 40-55 wt %, or 45-70 wt %, or 45-65 wt %, or 45-60 wt %, or 50-70 wt %, or 50-65 wt %.

The person of ordinary skill in the art can otherwise perform the cyclic dehydrogenation processes and adapt the systems therefor using their skill and judgment, based on the disclosure herein. The person of ordinary skill in the art can apply any applicable embodiment of any cyclic dehydrogenation process or system known in the art, including those described in each of the following disclosures: U.S. Pat. Nos. 2,419,997, 2,423,029, 7,622,623, 7,973,207, and 8,188,328, and U.S. Patent Application Publication no. 2023/0090285.

The processes as described herein can be used for alkane dehydrogenation. Accordingly, in various embodiments as otherwise described herein, the alkane stream comprises at least 50 wt % $C_2$-$C_6$ alkanes, as a percentage to total hydrocarbons (e.g., at least 60 wt %, or at least 75 wt %, or at least 85 wt %, or at least 90 wt %). For example, in particular embodiments, the alkane stream comprises at least 50 wt % $C_2$-$C_4$ alkanes, as a percentage to total hydrocarbons (e.g., at least 60 wt %, or at least 75 wt %, or at least 85 wt %, or at least 90 wt %). The person of ordinary skill in the art will appreciate that a wide variety of alkane streams, including, for example, those described in the references described above. In various embodiments, the alkane stream includes air, at an air to hydrocarbon ratio in the range of 2-7% (weight air/weight hydrocarbon).

Various dehydrogenation catalysts are known in the art. For example, in various embodiments as otherwise described herein, the dehydrogenation catalyst(s) of the one or more hybrid catalyst beds comprises chromium, e.g., in the form of an oxide. For example, in various embodiments, the chromium oxide is present in an amount of 5 wt % to 40 wt % of the dehydrogenation catalyst, calculated as $Cr_2O_3$. In various embodiments, the catalyst may be a supported catalyst. For example, in various embodiments, the dehydrogenation catalyst comprises an alumina support. In various embodiments, the dehydrogenation catalyst is produced by impregnation, co-mixing, or sol-gel methods. Particular dehydrogenation catalysts include those having chromium (15-30 wt % calculated as $Cr_2O_3$), sodium (0.1-1.5 wt %, calculated as oxide), potassium (0.1-3 wt % calculated as oxide), zirconium (0.1-2 wt % calculated as $ZrO_2$) and magnesium (0.3-1 wt % calculated as oxide), all on an alumina carrier.

But other dehydrogenation catalysts are known for use in cyclic dehydrogenation processes, and the person of ordinary skill in the art, based on the disclosure herein and the state of the art in cyclic dehydrogenations, can adapt these catalysts for use in the processes described herein. For example, U.S. Patent Application Publication no. 2023/0090285 a particulate dehydrogenation catalyst comprising a primary species P1 selected from Ga, In, Tl, Ge, Sn, Pb, and any mixture thereof as an active metal, disposed on a support. Such dehydrogenation catalysts can be used in the processes described herein.

Various heat-generating materials are known in the art. For example, in various embodiments as otherwise described herein, the heat-generating material comprises a metal at a concentration of 2 wt % to 40 wt % of the total heat-generating material. In various embodiments, the metal of the heat-generating material comprises at least one of copper, chromium, molybdenum, vanadium, cerium, yttrium, scandium, tungsten, manganese, iron, cobalt, nickel, silver, or bismuth. The metal of the heat-generating material can be provided as metal, oxide, or any combination thereof. In some embodiments, the heat-generating material further comprises a promoter such as an alkali metal, an alkaline earth metal, or zirconium. Further details regarding heat-generating materials can be found in U.S. Pat. Nos. 7,622,623, 7,973,207, and 8,188,328, and U.S. Patent Application Publication no. 2023/0090285. The person of ordinary skill in the art can adapt the heat-generating materials described herein for use in the processes and systems described here. One particular heat-generating material includes calcium (5-25 wt % calculated as oxide), magnesium (0.2-2 wt %, calculated as oxide), sodium (0.2-2 wt %, calculated as oxide), potassium (0.2-2 wt %, calculated as oxide), manganese (0.1-10 wt %, calculated as oxide), and copper (2-25 wt % calculated as CuO). Various examples of heat-generating materials include copper oxide, copper aluminate, calcium sulfate, copper sulfate, zinc oxide, nickel oxide, iron oxide, tin oxide, cobalt oxide, vanadium oxide, lanthanum oxide, cerium oxide and manganese oxide, which can be supported on an appropriate support. Another particular example of a heat-generating material is copper oxide supported on alumina, in which the copper oxide comprises at least about 8 wt % of the heat-generating inert component.

The one or more hybrid catalyst beds can also include, in addition to the dehydrogenation catalyst and the heat-generating material, a granular inert material, such as an alumina material, e.g., a granular alpha-alumina. Of course, other inert materials can be used. The inert can act as a heat sink and thus can help to maintain heat in the hybrid catalyst bed by providing thermal mass.

While certain desirable relative amounts of heat-generating material in the one or more hybrid catalyst beds are described above, the person of ordinary skill in the art will appreciate that other amounts can be used. For example, in various embodiments, one or more of the one or more hybrid catalyst beds includes 15-70 wt % of dehydrogenation catalyst, e.g., 15-50 wt %, or 15-40 wt %, or 15-30 wt % (i.e., as a fraction of total amount of dehydrogenation catalyst, heat-generating material, and inert). In various embodiments, one or more of the one or more hybrid catalyst beds includes 15-70 wt %, of heat-generating material, e.g., 15-65 wt %, or 15-60 wt %, or 15-55 wt %, or 15-50 wt %, or 15-45 wt %, or 15-40 wt %, or 15-35 wt %, or 15-30 wt %, or 25-70 wt %, or 25-65 wt %, or 55-60 wt %, or 25-55 wt %, or 25-50 wt %, or 25-45 wt %, or 25-40 wt %, or 35-70 wt %, or 35-65 wt %, or 35-60 wt %, or 35-55 wt %, or 35-50 wt % (i.e., as a fraction of total amount of dehydrogenation catalyst, heat-generating material, and inert). In various embodiments, one or more of the one or more hybrid catalyst beds includes up to 70 wt % inert, e.g., up to 65 wt %, or up to 60 wt %, or up to 55 wt %, or up to 50 wt %, or up to 45 wt %, or up to 40 wt %, or up to 35 wt %, or up to 30 wt % (i.e., as a fraction of total amount of dehydrogenation catalyst, heat-generating material, and inert).

The reducing gas stream for the reduction of the catalyst can be provided as is conventional in the art. For example, in various embodiments as otherwise described herein, the reducing gas stream comprises hydrogen gas, optionally provided with an inert gas such as nitrogen. The reduction of the dehydrogenation catalyst can generally be performed as described in any applicable embodiment of the references described above.

The oxygen-containing stream can be provided by the person of ordinary skill in the art in view of the teachings herein and of the state of the art. In various embodiments, the oxygen-containing gas is substantially made of air (e.g., at least 50 wt %, at least 75 wt %, or at least 90 wt % air). But other oxygen-containing streams can be used. Desirably, the oxygen-containing stream includes at least 5 wt % oxygen, e.g., at least 10 wt %.

The person of ordinary skill in the art can provide reaction conditions based on the particular system used, in view of the state of the art, including reaction conditions described in any embodiment of the references identified above. In various embodiments, the dehydrogenation is performed at a dehydrogenation temperature in the range of 520-680° C., a liquid hourly space velocity in the range of 0.8-2.5 $h^{-1}$, and a pressure in the range of 0.2-2 bar. Of course, the person of ordinary skill in the art will appreciate that a wide variety of reaction conditions can be applied.

Various exemplary embodiments of the disclosure include, but are not limited to the enumerated embodiments listed below, which can be combined in any number and in any combination that is not technically or logically inconsistent.

Embodiment 1. A process for the dehydrogenation of hydrocarbons, the process comprising:

- providing a dehydrogenation reactor comprising one or more hybrid catalyst beds, each of the one or more hybrid catalyst beds comprising a dehydrogenation catalyst, a heat-generating material, and, optionally, a granular inert material;
- performing the following cycle of steps a plurality of times:
  - reducing the one or more hybrid catalyst beds by flowing therethrough a reducing stream comprising hydrogen; then
  - contacting the one or more hybrid catalyst beds with an alkane stream by flowing from an upstream direction to a downstream direction, to dehydrogenate the alkane stream to provide an alkene stream, the dehydrogenation being endothermic; then
  - purging the one or more hybrid catalyst beds, for example, at least 50 wt %, or at least 75 wt %, or at least 90 wt %, (e.g., with a steam stream) to substantially remove hydrocarbon therefrom; then
  - contacting the one or more hybrid catalyst beds with an oxygen-containing stream by introducing the oxygen-containing stream to the dehydrogenation reactor, at a first temperature sufficient to regenerate the one or more hybrid catalyst beds (for example, by removing a substantial degree (e.g., at least 50 wt %, or at least 75 wt %, or at least 90 wt %) of coke and other deposits), while monitoring at least one temperature of at least one of the one or more hybrid catalyst beds,
- wherein at least one of the reducing of the one or more hybrid catalyst beds and the regeneration of the one or more hybrid catalyst beds causes the heat-generating material to generate heat, and
- wherein the process further comprises, when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes (e.g., within two minutes, or within a minute).

Embodiment 2. A process for the dehydrogenation of hydrocarbons, the process comprising:

- providing a dehydrogenation reactor comprising one or more hybrid catalyst beds, each of the one or more hybrid catalyst beds comprising a dehydrogenation catalyst, a heat-generating material, and, optionally, a granular inert material;
- performing the following cycle of steps a plurality of times:
  - reducing the one or more hybrid catalyst beds by flowing therethrough a reducing stream comprising hydrogen; then
  - contacting the one or more hybrid catalyst beds with an alkane stream by flowing from an upstream direction to a downstream direction, to dehydrogenate the alkane stream to provide an alkene stream, the dehydrogenation being endothermic; then
  - purging the one or more hybrid catalyst beds (e.g., with a steam stream) to substantially remove hydrocarbon therefrom; then
  - contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring at least one temperature of at least one of the one or more hybrid catalyst beds,
- wherein at least one of the reducing of the one or more hybrid catalyst beds and the regeneration of the one or more hybrid catalyst beds causes the heat-generating material to generate heat, and
- wherein the process further comprises, when the temperature of at least one of the hybrid catalyst beds becomes higher than a first threshold value during a number of consecutive cycles greater than a second threshold value, reducing the temperature of the oxygen-containing stream such that the temperature of the at least one of the hybrid catalyst beds is reduced by a third value per cycle (e.g., 2° C. per cycle, e.g., by at least 5° C. per cycle, or at least 10° C. per cycle), for a plurality of cycles.

Embodiment 3. The process of embodiment 2, wherein the reduction of temperature of the oxygen-containing stream is performed with a temperature drop of at least 50° C. within three minutes (e.g., within two minutes, or within a minute).

Embodiment 4. The process of any of embodiments 1-3, wherein at least a portion of the oxygen-containing stream is provided by heating a first input stream comprising oxygen (e.g., using a heater) to provide a hotter oxygen-containing substream having a temperature, and providing the oxygen-containing substream as at least a portion of the oxygen-containing stream.

Embodiment 5. The process of embodiment 4, wherein the hotter air stream makes up at least 90 wt % (e.g., at least 95 wt % or at least 99 wt %) of the oxygen-containing stream during at least one stage of the regeneration, for example, during at least one period in which the monitored temperature of the one or more hybrid catalyst bed is below the first threshold value.

Embodiment 6. The process of embodiment 4 or embodiment 5, wherein the reduction of the temperature of the oxygen-containing stream comprises admixing with the hotter oxygen-containing substream a colder oxygen-containing substream having a temperature substantially lower than the temperature of the hotter oxygen-containing stream.

Embodiment 7. The process of embodiment 6, wherein the hotter oxygen-containing substream and the colder oxygen-containing substream are admixed before introduction to the reactor, e.g., in a mixing zone.

Embodiment 8. The process of embodiment 4 or embodiment 5, wherein the reduction of the temperature of the oxygen-containing stream is provided by introducing to the reactor a colder oxygen-containing substream having a temperature substantially lower than the temperature of the hotter oxygen-containing stream.

Embodiment 9. The process of any of embodiments 4-8, wherein the hotter oxygen-containing substream and the colder oxygen-containing substream are provided from a common oxygen-containing gas source.

Embodiment 10. The process of any of embodiments 1-9, wherein during at least one stage of the regeneration, for example, during at least one period in which the monitored temperature of the one or more hybrid catalyst bed is below the first threshold value, the oxygen-containing stream has a temperature in the range of 500° C. to 800° C. (e.g., in the range 550° C. to 800° C., or 600° C. to 800° C., or 500° C. to 750° C., or 500° C. to 700° C.).

Embodiment 11. The process of any of embodiments 1-10, wherein when the temperature of at least one of the hybrid catalyst beds becomes higher than the first threshold value, the temperature of the oxygen-containing stream is reduced by at least 75° C., the reduction of temperature occurring with a temperature drop of at least 75° C. within three minutes (e.g., within two minutes, or within a minute).

Embodiment 12. The process of any of embodiments 1-10, wherein when the temperature of at least one of the hybrid catalyst beds becomes higher than the first threshold value, the temperature of the oxygen-containing stream is reduced by at least 100° C., the reduction of temperature occurring with a temperature drop of at least 100° C. within three minutes (e.g., within two minutes, or within a minute).

Embodiment 13. The process of any of embodiments 4-12, wherein the temperature of the hotter oxygen-containing substream is in the range of 500° C. to 800° C. (e.g., in the range 550° C. to 800° C., or 600° C. to 800° C., or 500° C. to 750° C., or 500° C. to 700° C.).

Embodiment 14. The process of any of embodiments 4-13, wherein the temperature of the colder oxygen-containing substream is in the range of −20° C. to 250° C., for example, in the range of 0° C. to 200° C., or 0° C. to 100° C., or 0° C. to 50° C.

Embodiment 15. The process of any of embodiments 1-14, wherein in a plurality of the cycles, the regeneration and the reduction steps are sufficient to raise the temperatures of the one or more hybrid catalyst beds by at least 90% of the temperature loss during the preceding dehydrogenation step, e.g., at least 95% of the temperature loss during the preceding dehydrogenation step, or at least 98% of the of the temperature loss during the preceding dehydrogenation step.

Embodiment 16. The process of any of embodiments 1-15, wherein the heat-generating material provides heat during at least the regeneration step.

Embodiment 17. The process of any of embodiments 1-16, wherein the heat generated by the heat-generating material during the reduction and/or regeneration steps contributes at least 40% of the heat energy consumed in the dehydrogenation step (e.g., at least 50%, or at least 60%).

Embodiment 18. The process of any of embodiments 1-16, wherein the heat generated by the heat-generating material during the reduction and/or regeneration steps contributes in the range of 40-85% of the energy consumed in the endothermic dehydrogenation reaction (e.g., in the range of 40-80%, or 40-75%, or 40-70%, or 50-85%, or 50-80%, or 50-75%, or 50-70%, or 60-85%, or 50-80%, or 50-75%).

Embodiment 19. The process of any of embodiments 1-18, wherein the heat energy provided to the one or more hybrid catalyst beds by the heat-generating material during the regeneration step is at least 40% of the total heat energy provided to the one or more hybrid catalyst beds by the heat-generating material and the oxygen-containing stream during the regeneration step (e.g., at least 50%, or at least 60%).

Embodiment 20. The process of any of embodiments 1-18, wherein the heat energy provided to the one or more hybrid catalyst beds by the heat-generating material during the regeneration step is in the range of 40-85% of the total heat energy provided to the one or more hybrid catalyst beds by the heat-generating material and the oxygen-containing stream during the regeneration step (e.g., in the range of 40-80%, or 40-75%, or 40-70%, or 50-85%, or 50-80%, or 50-75%, or 50-70%, or 60-85%, or 50-80%, or 50-75%).

Embodiment 21. The process of any of embodiments 1-20, wherein the oxygen-containing stream further comprises a fuel gas.

Embodiment 22. The process of any of embodiments 1-21, wherein one or more of (e.g., each of) the one or more hybrid catalyst beds includes heat-generating material in an amount that is at least 40 wt % of the combined amount of heat-generating material and dehydrogenation catalyst, e.g., at least 45 wt %, or at least 50 wt %.

Embodiment 23. The process of any of embodiments 1-21, wherein one or more of (e.g., each of) the one or more hybrid catalyst beds includes heat-generating material in an amount in the range of 40-70 wt % of the combined amount of heat-generating material and dehydrogenation catalyst, e.g., 40-65 wt %, or 40-60 wt %, or 40-55 wt %, or 45-70 wt %, or 45-65 wt %, or 45-60 wt %, or 50-70 wt %, or 50-65 wt %.

Embodiment 24. A system for the dehydrogenation of hydrocarbons, the system comprising:

a dehydrogenation reactor comprising one or more hybrid catalyst beds, each of the one or more hybrid catalyst beds comprising a dehydrogenation catalyst and a heat-generating material, the heat-generating material being configured to generate heat in response to at least one of a reducing of the hybrid catalyst bed in which it is disposed and regeneration of the hybrid catalyst bed in which it is disposed;

a source of a reducing gas stream comprising hydrogen, operatively coupled to the one or more hybrid catalyst beds; and a source of an alkane stream, operatively coupled to the at least one hybrid catalyst bed and configured to flow from an upstream direction to a downstream direction of the dehydrogenation reactor; and a source of an oxygen-containing stream operatively coupled to the one or more hybrid catalyst beds, through an operative coupling to the dehydrogenation reactor;

one or more temperature sensors, each independently operatively coupled to one of the one or more hybrid catalyst beds; and a control system configured such that when a temperature of at least one of the hybrid catalyst beds becomes higher than a first threshold value as measured by at least one of the one or more temperature sensors during a number of consecutive cycles greater than a second threshold value, the temperature of the oxygen-containing stream at the first input can be reduced (a) by at least 50° C., the reduction of temperature occurring with a temperature drop of at least 50° C. within three minutes (e.g., within two minutes, or within a minute); and/or (b) such that the temperature of the at least one of the hybrid catalyst beds is reduced by at least a third value per cycle (e.g., 2° C. per cycle, e.g., by at least 5° C. per cycle, or at least 10° C. per cycle), for a plurality of cycles.

Embodiment 25. A system for the dehydrogenation of hydrocarbons, the system comprising:

- a dehydrogenation reactor comprising one or more hybrid catalyst beds, each of the one or more hybrid catalyst beds comprising a dehydrogenation catalyst and a heat-generating material, the heat-generating material being configured to generate heat in response to at least one of a reducing of the hybrid catalyst bed in which it is disposed and regeneration of the hybrid catalyst bed in which it is disposed;
- a source of a reducing gas stream comprising hydrogen, operatively coupled to the one or more hybrid catalyst beds; and
- a source of an alkane stream, operatively coupled to the at least one hybrid catalyst bed and configured to flow from an upstream direction to a downstream direction of the dehydrogenation reactor; and
- a source of a hotter oxygen-containing substream and a source of a colder oxygen-containing substream, each operatively coupled to the one or more hybrid catalyst beds through operative coupling to the dehydrogenation reactor, configured to allow for a selection of a variable flow ratio of the hotter oxygen-containing substream to the colder oxygen-containing substream.

Embodiment 26. The system of embodiment 25, further comprising:

- one or more temperature sensors, each independently operatively coupled to one of the one or more hybrid catalyst beds; and
- a control system configured such that when a temperature of at least one of the hybrid catalyst beds becomes higher than a first threshold value as measured by at least one of the one or more temperature sensors during a number of consecutive cycles greater than a second threshold value, the temperature of the oxygen-containing stream at the first input by can be reduced by adjusting the variable flow ratio of the hotter oxygen-containing substream to the colder oxygen-containing substream, (a) the reduction of temperature occurring with a temperature drop of at least 50° C. within three minutes (e.g., within two minutes, or within a minute); and/or (b) such that the temperature of the at least one of the hybrid catalyst beds is reduced by at least a third value per cycle (e.g., 2° C. per cycle, e.g., by at least 5° C. per cycle, or at least 10° C. per cycle), for a plurality of cycles.

Embodiment 27. The system of embodiment 25 or embodiment 26, wherein the system includes a source of a first input stream comprising oxygen; a heater configured to heat the first input stream to provide a hotter oxygen-containing substream having a temperature, and is configured to provide the hotter oxygen-containing substream as at least a portion of the oxygen-containing stream.

Embodiment 28. The system of any of embodiments 25-27, wherein the source of the hotter oxygen-containing substream and the source of the colder oxygen-containing substream are configured to be mixed before introduction to the dehydrogenation reactor.

Embodiment 29. The system of embodiment 28, wherein the system comprises as the source of the hotter oxygen-containing substream a heater configured to heat an oxygen-containing gas, and a mixing zone in which the hotter oxygen-containing substream and the colder oxygen-containing substream are mixed.

Embodiment 30. The system of any of embodiments 25-27, wherein the hotter oxygen-containing substream and the colder oxygen-containing substream are configured to be introduced into the dehydrogenation reactor separately.

Embodiment 31. The system of embodiment 30, wherein the dehydrogenation reactor further comprises a first substream inlet coupled to the source of the hotter oxygen-containing substream and a second substream inlet coupled to the source of the colder oxygen-containing substream.

Embodiment 32. The system of any of embodiments 24 and 26-31, wherein the control system is configured such that when the temperature of at least one of the hybrid catalyst beds becomes higher than the first threshold value, the temperature of the oxygen-containing stream can be reduced by at least 75° C., the reduction of temperature occurring with a temperature drop of at least 75° C. within three minutes (e.g., within two minutes, or within a minute).

Embodiment 33. The system of any of embodiments 24 and 26-31, wherein the control system is configured such that when the temperature of at least one of the hybrid catalyst beds becomes higher than the first threshold value, the temperature of the oxygen-containing stream can be reduced by at least 100° C., the reduction of temperature occurring with a temperature drop of at least 100° C. within three minutes (e.g., within two minutes, or within a minute).

Embodiment 34. The system of any of embodiments 24-33, configured to perform a process according to any of embodiments 1-23.

Embodiment 35. The process or system of any of embodiments 1-34, wherein the alkane stream comprises at least 50 wt % $C_2$-$C_6$ alkanes, as a percentage to total hydrocarbons (e.g., at least 60 wt %, or at least 75 wt %, or at least 85 wt %, or at least 90 wt %).

Embodiment 36. The process or system of any of embodiments 1-34, wherein the alkane stream comprises at least 50 wt % $C_2$-$C_4$ alkanes, as a percentage to total hydrocarbons (e.g., at least 60 wt %, or at least 75 wt %, or at least 85 wt %, or at least 90 wt %).

Embodiment 37. The process or system of any of embodiments 1-36, wherein the dehydrogenation catalyst of the one or more hybrid catalyst beds comprises chromium, e.g., in the form of chromium oxide.

Embodiment 38. The process or system of embodiment 37, wherein the chromium oxide is present in an amount of 5 wt % to 40 wt % of the dehydrogenation catalyst, calculated as $Cr_2O_3$.

Embodiment 39. The process or system of any of embodiments 1-38, wherein the dehydrogenation catalyst comprises an alumina support.

Embodiment 40. The process or system of any of embodiments 1-39, wherein the heat-generating material comprises a metal at a concentration of 2 wt % to 40 wt % of the total heat-generating material.

Embodiment 41. The process or system of embodiment 40, wherein the metal comprises at least one of copper, chromium, molybdenum, vanadium, cerium, yttrium, scandium, tungsten, manganese, iron, cobalt, nickel, silver, or bismuth.

Embodiment 42. The process or system of any of embodiments 1-41, wherein the heat-generating material comprises a promoter, wherein the promoter comprises an alkali metal, an alkaline earth metal, or zirconium.

Embodiment 43. The process or system of any of embodiments 1-42, wherein the granular inert material is present in the one or more catalyst beds.

Embodiment 44. The process or system of any of embodiments 1-43, wherein the granular inert material is a granular alumina, such as granular alpha-alumina.

Embodiment 45. The process or system of any of embodiments 1-24 and 26-41, wherein the first threshold value is at least 600° C., e.g., in the range of 600-1100° C.

Embodiment 46. The process or system of any of embodiments 1-24 and 26-41, wherein the first threshold value is in the range of 500-1050° C., or 500-1000° C., or 500-950° C., or 500-900° C., or 500-850° C., or 500-800° C., or 500-750° C., or 500-700° C., or 500-650° C., or 500-600° C.

Embodiment 47. The process or system of any of embodiments 1-24 and 26-41, wherein the first threshold value is at least 550° C., for example, in the range of 550-1100° C., e.g., 550-1050° C., or 550-1000° C., or 550-950° C., or 550-900° C., or 550-850° C., or 550-800° C., or 550-750° C., or 550-700° C., or 550-650° C.

Embodiment 48. The process or system of any of embodiments 1-24 and 26-41, wherein the first threshold value is in the range of 600-1050° C., or 600-1000° C., or 600-950° C., or 600-900° C., or 600-850° C., or 600-800° C., or 600-750° C., or 600-700° C.

Embodiment 49. The process or system of any of embodiments 1-24 and 26-41, wherein the first threshold value is at least 650° C., for example, in the range of 650-1100° C., e.g., 650-1050° C., or 650-1000° C., or 650-950° C., or 650-900° C., or 650-850° C., or 650-800° C., or 650-750° C.

Embodiment 50. The process or system of any of embodiments 1-24 and 26-41, wherein the first threshold value is at least 700° C., for example, in the range of 700-1100° C., e.g., 700-1050° C., or 700-1000° C., or 700-950° C., or 700-900° C., or 700-850° C., or 700-800° C.

Embodiment 51. The process or system of any of embodiments 1-24 and 26-41, wherein the first threshold value is at least 750° C., for example, in the range of 750-1100° C., e.g., 750-1050° C., or 750-1000° C., or 750-950° C., or 750-900° C., or 750-850° C.

Embodiment 52. The process or system of any of embodiments 1-24 and 26-41, wherein the first threshold value is at least 800° C., for example, in the range of 800-1100° C., e.g., 800-1050° C., or 800-1000° C., or 800-950° C., or 800-900° C.

Embodiment 53. The process or system of any of embodiments 1-24 and 26-41, wherein the first threshold value is at least 850° C., for example, in the range of 850-1100° C., e.g., 850-1050° C., or 850-1000° C., or 850-950° C.

Embodiment 54. The process or system of any of embodiments 1-24 and 26-53, wherein the second threshold value is at least 5, e.g., at least 7.

Embodiment 55. The process or system of any of embodiments 1-24 and 26-53, wherein the second threshold value is at least 10, e.g., at least 20.

Embodiment 56. The process or system of any of embodiments 1-24 and 26-55, wherein the second threshold value is no more than 100, e.g., no more than 75.

Embodiment 57. The process or system of any of embodiments 1-24 and 26-55, wherein the second threshold value is no more than 50, e.g., no more than 25.

Embodiment 58. The process or system of any of embodiments 1-24 and 26-53, wherein the second threshold value is in the range of 5-100, e.g., in the range of 5-75, or 5-50, or 5-25, or 7-100, or 7-75, or 7-50, or 7-35, or 10-100, or 10-75, or 10-50, or 10-25, or 20-100, or 20-75, or 20-50.

Embodiment 59. The process or system of any of embodiments 1-24 and 26-53, wherein the third value is at least 2° C., e.g., in the range of 0.2-50° C., or 2-30° C., or 2-15° C., or 2-10° C., or 2-5° C.

Embodiment 60. The process or system of any of embodiments 1-24 and 26-53, wherein the third value is at least 5° C., e.g., in the range of 0.5-50° C., or 5-30° C., or 5-15° C., or 5-10° C.

Embodiment 61. The process or system of any of embodiments 1-24 and 26-53, wherein the third value is at least 10° C., e.g., in the range of 10-50° C., or 10-30° C., or 10-20° C.

The particulars shown herein are by way of example and for purposes of illustrative discussion of certain embodiments of the present disclosure only and are presented in the cause of providing what is believed to be the most useful and readily understood description of the principles and conceptual aspects of various embodiments of the disclosure. In this regard, no attempt is made to show details associated with the methods of the disclosure in more detail than is necessary for the fundamental understanding of the methods described herein, the description taken with the examples making apparent to those skilled in the art how the several forms of the methods of the disclosure may be embodied in practice. Thus, before the disclosed processes and devices are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the methods of the disclosure (especially in the context of the following embodiments and claims) are to be construed to cover both the singular and the plural, unless otherwise indicated herein or clearly contradicted by context.

All percentages, ratios and proportions herein are by weight, unless otherwise specified.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Some embodiments of various aspects of the disclosure are described herein, including the best mode known to the inventors for carrying out the methods described herein. Of course, variations on these described embodiments will become apparent to those of ordinary skill in the art upon reading the foregoing description. The skilled artisan will employ such variations as appropriate, and as such the methods of the disclosure can be practiced otherwise than specifically described herein. Accordingly, the scope of the disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The phrase "at least a portion" as used herein is used to signify that, at least, a fractional amount is required, up to the entire possible amount.

In closing, it is to be understood that the various embodiments herein are illustrative of the methods of the disclosures. Other modifications that may be employed are within the scope of the disclosure. Thus, by way of example, but not of limitation, alternative configurations of the methods may be utilized in accordance with the teachings herein. Accordingly, the methods of the present disclosure are not limited to that precisely as shown and described.

We claim:

1. A process for the dehydrogenation of hydrocarbons, the process comprising:

providing a dehydrogenation reactor comprising one or more hybrid catalyst beds, each of the one or more hybrid catalyst beds comprising a dehydrogenation catalyst, a heat-generating material, and, optionally, a granular inert material;

performing the following cycle of steps a plurality of times:

reducing the one or more hybrid catalyst beds by flowing therethrough a reducing stream comprising hydrogen; then contacting the one or more hybrid catalyst beds with an alkane stream by flowing from an upstream direction to a downstream direction, to dehydrogenate the alkane stream to provide an alkene stream, the dehydrogenation being endothermic; then purging the one or more hybrid catalyst beds to substantially remove hydrocarbon therefrom; then contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring at least one temperature of at least one of the one or more hybrid catalyst beds, wherein at least one of the reducing of the one or more hybrid catalyst beds and the regeneration of the one or more hybrid catalyst beds causes the heat-generating material to generate heat, and wherein the process further comprises, when the temperature of at least one of the hybrid catalyst beds becomes higher than a first threshold value during a number of consecutive cycles greater than a second threshold value, reducing the temperature of the oxygen-containing stream by at least 50° C., the reduction of temperature occurring with a temperature drop of at least 50° C. within three minutes.

2. A process for the dehydrogenation of hydrocarbons, the process comprising:

providing a dehydrogenation reactor comprising one or more hybrid catalyst beds, each of the one or more hybrid catalyst beds comprising a dehydrogenation catalyst, a heat-generating material, and, optionally, a granular inert material;

performing the following cycle of steps a plurality of times:

reducing the one or more hybrid catalyst beds by flowing therethrough a reducing stream comprising hydrogen; then contacting the one or more hybrid catalyst beds with an alkane stream by flowing from an upstream direction to a downstream direction, to dehydrogenate the alkane stream to provide an alkene stream, the dehydrogenation being endothermic; then purging the one or more hybrid catalyst beds to substantially remove hydrocarbon therefrom; then contacting the one or more hybrid catalyst beds with an oxygen-containing stream by introducing the oxygen-containing stream to the dehydrogenation reactor, at a first temperature sufficient to regenerate the one or more hybrid catalyst beds, while monitoring at least one temperature of at least one of the one or more hybrid catalyst beds, wherein at least one of the reducing of the one or more hybrid catalyst beds and the regeneration of the one or more hybrid catalyst beds causes the heat-generating material to generate heat, and wherein the process further comprises, when the temperature of at least one of the hybrid catalyst beds becomes higher than a first threshold value during a number of consecutive cycles greater than a second threshold value, reducing the temperature of the oxygen-containing stream such that the temperature of the at least one of the hybrid catalyst beds is reduced by a third value per cycle, for a plurality of cycles.

3. The process of claim 2, wherein the reduction of temperature of the oxygen-containing stream is performed with a temperature drop of at least 50° C. within three minutes.

4. The process of claim 3, wherein the hotter air stream makes up at least 90 wt % of the oxygen-containing stream during at least one stage of the regeneration during at least one period in which the monitored temperature of the one or more hybrid catalyst bed is below the first threshold value.

5. The process of claim 1, wherein the reduction of the temperature of the oxygen-containing stream comprises admixing with a hotter oxygen-containing substream a colder oxygen-containing substream having a temperature substantially lower than the temperature of the hotter oxygen-containing stream.

6. The process of claim 1, wherein the reduction of the temperature of the oxygen-containing stream is provided by introducing to the reactor a colder oxygen-containing substream having a temperature substantially lower than the temperature of a hotter oxygen-containing stream being introduced to the reactor.

7. The process of claim 1, wherein during at least one stage of the regeneration, for example, during at least one period in which the monitored temperature of the one or more hybrid catalyst bed is below the first threshold value, the oxygen-containing stream has a temperature in the range of 500° C. to 800° C.

8. The process of claim 1, wherein when the temperature of at least one of the hybrid catalyst beds becomes higher than the first threshold value, the temperature of the oxygen-containing stream is reduced by at least 75° C., the reduction of temperature occurring with a temperature drop of at least 75° C. within three minutes.

9. The process of claim 1, wherein when the temperature of at least one of the hybrid catalyst beds becomes higher than the first threshold value, the temperature of the oxygen-containing stream is reduced by at least 100° C., the reduction of temperature occurring with a temperature drop of at least 100° C. within three minutes.

10. The process of claim 1, wherein in a plurality of the cycles, the regeneration and the reduction steps are sufficient to raise the temperatures of the one or more hybrid catalyst beds by at least 90% of the temperature loss during the preceding dehydrogenation step.

11. The process of claim 1, wherein the alkane stream comprises at least 90 wt % $C_2$-$C_4$ alkanes, as a percentage to total hydrocarbons.

12. The process of claim 1, wherein the first threshold value is at least 600° C.

13. The process of claim 1, wherein the second threshold value is at least 5.

14. The process of claim 2, wherein the third value is at least 5° C.

15. The process of claim 2, wherein the alkane stream comprises at least 90 wt % $C_2$-$C_4$ alkanes, as a percentage to total hydrocarbons;

the first threshold value is at least 600° C.;

the second threshold value is at least 5; and the third value is at least 5° C.

16. A system for the dehydrogenation of hydrocarbons, the system comprising:

a dehydrogenation reactor comprising one or more hybrid catalyst beds, each of the one or more hybrid catalyst beds comprising a dehydrogenation catalyst and a heat-generating material, the heat-generating material being configured to generate heat in response to at least one of a reducing of the hybrid catalyst bed in which it is disposed and regeneration of the hybrid catalyst bed in which it is disposed;

a source of a reducing gas stream comprising hydrogen, operatively coupled to the one or more hybrid catalyst beds; and a source of an alkane stream, operatively coupled to the at least one hybrid catalyst bed and configured to flow from an upstream direction to a downstream direction of the dehydrogenation reactor; and a source of an oxygen-containing stream operatively coupled to the one or more hybrid catalyst beds, through an operative coupling to the dehydrogenation reactor;

one or more temperature sensors, each independently operatively coupled to one of the one or more hybrid catalyst beds; and a control system configured such that when a temperature of at least one of the hybrid catalyst beds becomes higher than a first threshold value as measured by at least one of the one or more temperature sensors during a number of consecutive cycles greater than a second threshold value, the temperature of the oxygen-containing stream at the first input can be reduced (a) by at least 50° C., the reduction of temperature occurring with a temperature drop of at least 50° C. within three minutes; and/or (b) such that the temperature of the at least one of the hybrid catalyst beds is reduced by at least a third value per cycle, for a plurality of cycles.

17. The system of claim 16, further comprising a source of a hotter oxygen-containing substream and a source of a colder oxygen-containing substream, each operatively coupled to the one or more hybrid catalyst beds through operative coupling to the dehydrogenation reactor, configured to allow for a selection of a variable flow ratio of the hotter oxygen-containing substream to the colder oxygen-containing substream.

18. The system of claim 16, wherein the system includes a source of a first input stream comprising oxygen; a heater configured to heat the first input stream to provide a hotter oxygen-containing substream having a temperature, and is configured to provide the hotter oxygen-containing substream as at least a portion of the oxygen-containing stream.

19. The system of claim 16, wherein the control system is configured such that when the temperature of at least one of the hybrid catalyst beds becomes higher than the first threshold value, the temperature of the oxygen-containing stream can be reduced by at least 100° C., the reduction of temperature occurring with a temperature drop of at least 100° C. within three minutes.

* * * * *